United States Patent [19]

Watanabe et al.

[11] Patent Number: 5,336,897
[45] Date of Patent: Aug. 9, 1994

[54] OPTICAL DATA TRANSMISSION APPARATUS FOR TRANSMITTING A SIGNAL BETWEEN A ROTATABLE PORTION AND FIXED PORTION OF AN X-RAY CT SCANNER

[75] Inventors: Naofumi Watanabe; Yasuo Nobuta, both of Tochigi, Japan

[73] Assignee: Kabushiki Kaisha Toshiba, Kawasaki, Japan

[21] Appl. No.: 3,658

[22] Filed: Jan. 13, 1993

[30] Foreign Application Priority Data

Jan. 14, 1992 [JP] Japan .................................. 4-005091
Aug. 5, 1992 [JP] Japan .................................. 4-208856

[51] Int. Cl.$^5$ ............................................. G02B 27/00
[52] U.S. Cl. ..................................... 250/551; 307/311
[58] Field of Search ................... 250/551; 378/15, 10, 378/19; 359/152, 159, 143; 385/25–26; 307/311

[56] References Cited

U.S. PATENT DOCUMENTS

| | | | |
|---|---|---|---|
| 4,310,767 | 1/1982 | Peacock | 250/551 |
| 4,401,360 | 8/1983 | Streckmann et al. | 250/551 |
| 4,438,425 | 3/1984 | Tsuchida et al. | 250/551 |
| 4,466,695 | 8/1984 | Kruger | 385/26 |
| 4,472,052 | 9/1984 | Lofgren | 250/551 |
| 4,996,435 | 2/1991 | Keller | 250/551 |
| 5,010,254 | 4/1991 | Moore | 250/551 |
| 5,016,961 | 5/1991 | Aldrich | 250/551 |
| 5,134,639 | 7/1992 | Vekstein et al. | 250/551 |

FOREIGN PATENT DOCUMENTS 0292919 11/1989 Japan ...................................... 385/26

Primary Examiner—David C. Nelms
Attorney, Agent, or Firm—Finnegan, Henderson, Farabow, Garrett & Dunner

[57] ABSTRACT

An optical data transmission apparatus which is used to transmit a signal between the rotating portion and fixed portion of an X-ray CT scanner comprises light emitting elements arranged on a side plane of the rotating portion which is perpendicular to a rotation axis and are uniformly driven according to transmission data to emit lights in a direction parallel to the rotation axis. A light receiving element is disposed on the side plane of the fixed portion which faces the light emitting elements. The interval between the light emitting elements is so set that the illumination areas formed by the light emitting elements partly overlap each other on the light receiving element. Therefore, the light receiving element always receives a light or lights from one or two of the light emitting elements during the rotation of the rotating portion and transmission data from all of the light emitting elements can be continuously transmitted to the light receiving element.

33 Claims, 9 Drawing Sheets

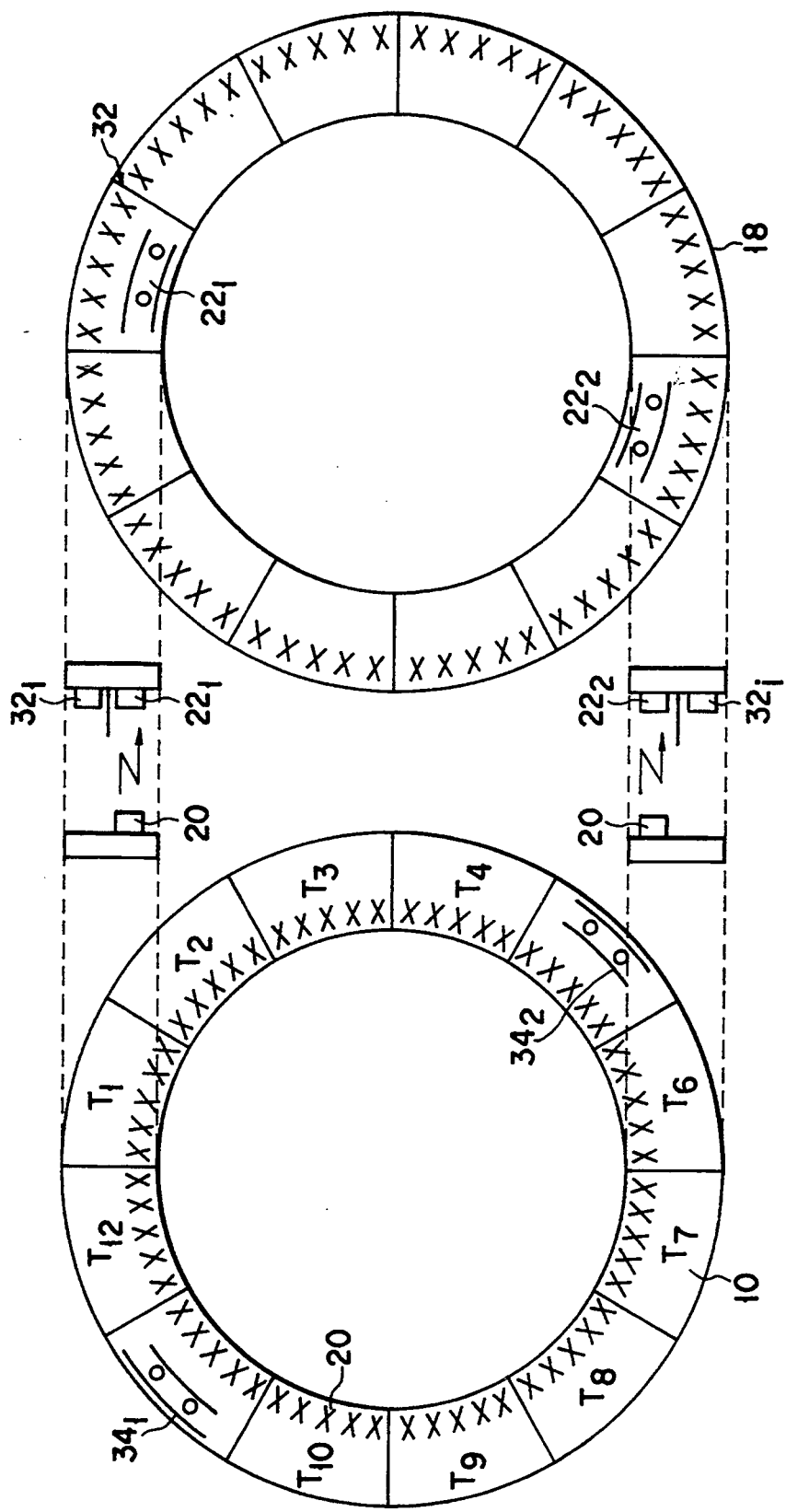
F I G. 6

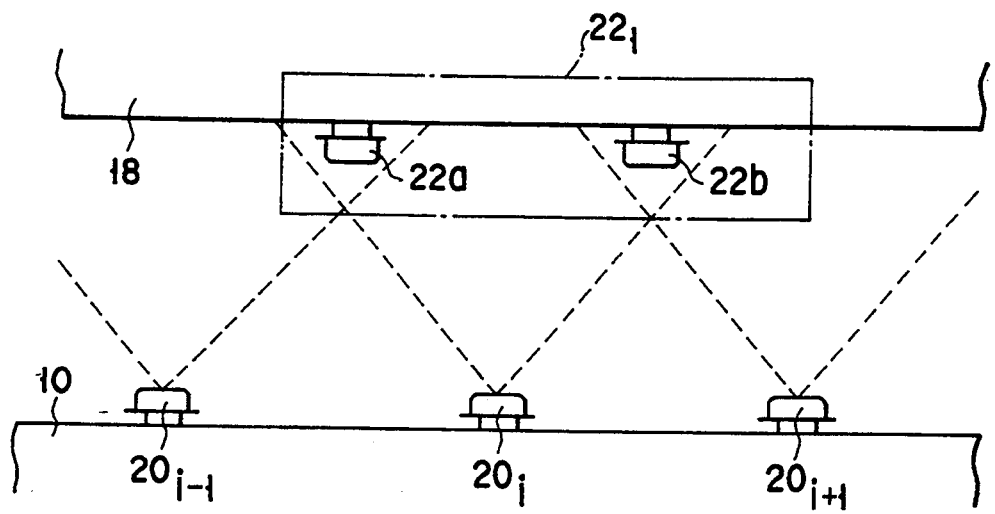
F I G. 8
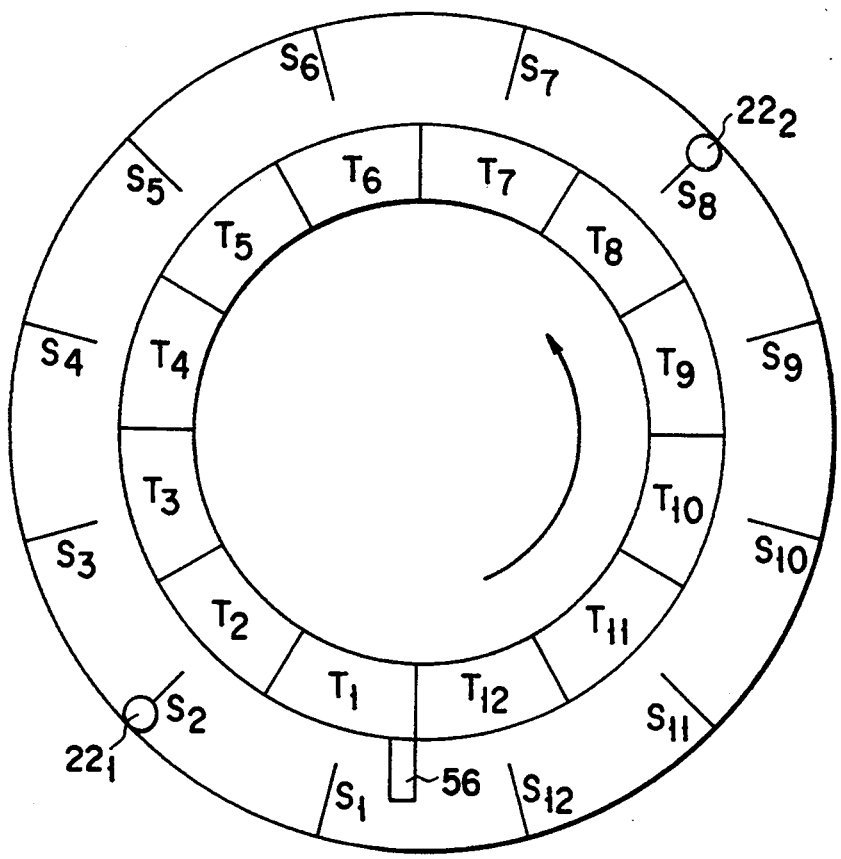
F I G. 9

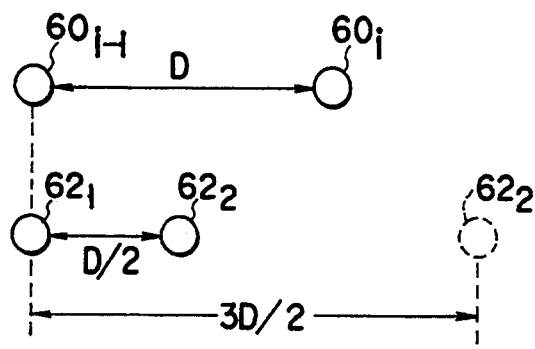
F I G. 13
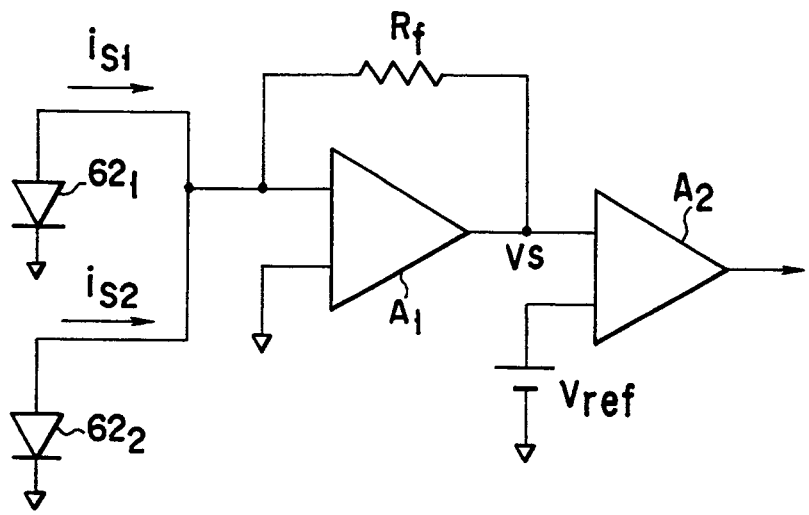
F I G. 14
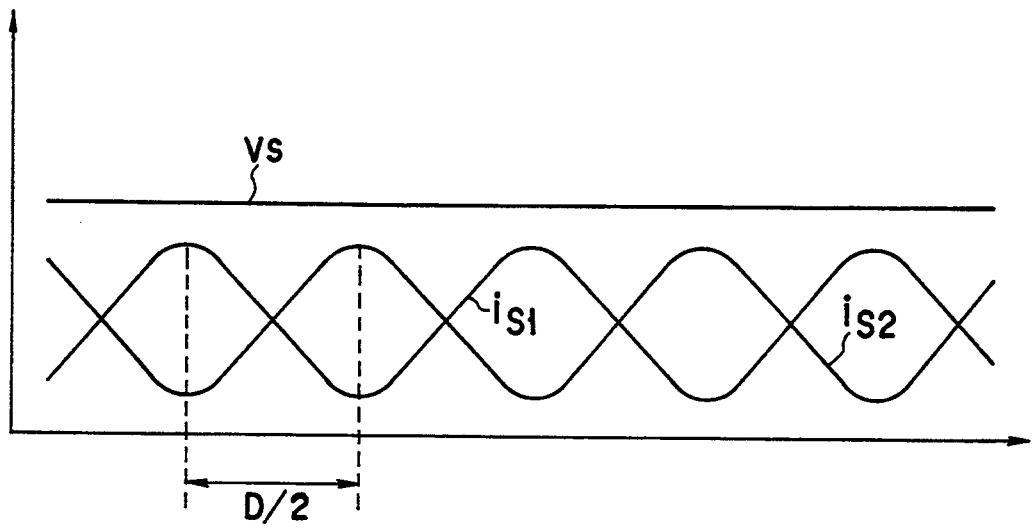
F I G. 15

OPTICAL DATA TRANSMISSION APPARATUS FOR TRANSMITTING A SIGNAL BETWEEN A ROTATABLE PORTION AND FIXED PORTION OF AN X-RAY CT SCANNER

BACKGROUND OF THE INVENTION

1. Field of the Invention

The present invention relates to an optical apparatus for transmitting data between two members whose positions are changed relative to each other, for example, an optical data transmission apparatus for transmitting data between a rotating portion and a fixed portion in a gantry of an X-ray computerized tomography (CT) scanner.

2. Description of the Related Art

Generally, in an X-ray CT scanner, data transmission between the rotating portion and the fixed portion in the gantry is effected via a slip ring. That is, a conductive metal is arranged in a ring form on the rotating portion side, a brush formed of a conductive member is disposed on the fixed portion side, and the brush is always set in contact with the ring irrespective of the rotation/stoppage of the rotating portion. Contact between the brush and the ring causes the rotating portion and the fixed portion to be electrically connected to each other, thereby making it possible to permit data to be transmitted between the rotating portion and the fixed portion during the rotation.

However, in the above slip ring system, since the brush is always set in mechanical contact with the ring, wear would occur in the mechanical contact portions thereof. Therefore, periodic maintenance is required and it is troublesome. Further, data transmission is sometimes instantly stopped (instantaneously interrupted) by the poor contact or contact resistance between the ring and the brush, thus lowering the reliability and data transmission quality. The amount of data to be transmitted is dependent on the number of rings and the ability (rate) of data transmission between the ring and the brush and the rate is limited. Therefore, in order to increase the amount of transmission data to exceed the limited value, the number of rings must be increased, and in this case, the size of the mechanism becomes large.

In order to overcome the above problems, an optical data transmission apparatus is recently developed as recited in U.S. Pat. No. 4,996,435 (Keller). This apparatus comprises plural light emitting elements disposed on the rotating portion side and a light receiving element disposed on the fixed portion side and faced toward the light emitting elements for receiving light emitted from at least one light emitting element. Since the light is emitted in a plane perpendicular to the axis of the patient or the rotating axis of the rotating portion, manufacturing of the apparatus is difficult. Surfaces of the rotating portion and the fixed portion facing each other are cylindrical surfaces. Therefore, it is difficult to dispose the light emitting elements and the light receiving element on the cylindrical surface.

The number of the data channel is one in this prior art. Plural items of data cannot be simultaneously transmitted. Therefore, it is difficult to effectively transmit a large amount of data.

Further, the distance between the light emitting element and the light receiving element periodically changes during the rotation of the rotating portion. Thus, the amount of light received by the light receiving element also periodically changes during the rotation. Therefore, it is necessary to increase the dynamic range of a receiver circuit in order to cope with this variation. However, the S/N ratio is decreased when the dynamic range is increased.

SUMMARY OF THE INVENTION

Accordingly, it is a first object of the present invention to provide a simple optical data transmission apparatus which can reliably transmit data and can be easily manufactured.

It is a second object of the present invention to provide an optical data transmission apparatus which is simple in construction and can effectively transmit a large amount of data.

It is a third object of the present invention to provide a simple optical data transmission apparatus which can reliably transmit data with a high S/N ratio.

According to the present invention, there is provided an optical data transmission apparatus comprising first and second members at least one of which rotates to change a relative relationship in position and which respectively have first and second planes perpendicular to a rotation axis; light emitting means, arranged at the first plane of the first member, for emitting light in accordance with transmission data; and light receiving means, arranged at the second plane of the second member, for receiving light emitted from the light emitting means.

According to another aspect of the present invention, there is provided an optical data transmission apparatus comprising first and second members at least one of which rotates to change a relative relationship in position, light emitting means, arranged at a plane of the first member which is perpendicular to a rotation axis, for emitting light in accordance with transmission data, and light receiving means, arranged at a plane of the second member other than a plane which is perpendicular to the rotation axis, for receiving light emitted from the light emitting means.

According to further aspect of the present invention, there is provided an optical data transmission apparatus comprising first and second members at least one of which rotates to change a relative relationship in position, light emitting means, arranged at a plane of the first member other than a plane which is perpendicular to a rotation axis, for emitting light in accordance with transmission data, and light receiving means, arranged at a plane of the second member which is perpendicular to the rotation axis, for receiving light emitted from the light emitting means.

According to still further aspect of the present invention, there is provided an optical data transmission apparatus comprising first and second members at least one of which rotates to change a relative relationship in position, light emitting means, arranged at the first member, for emitting light in accordance with transmission data in a direction other than a direction perpendicular to the rotation axis, and light receiving means, arranged at the second member, for receiving light emitted from the light emitting means.

According to still another aspect of the present invention, there is provided an optical data transmission apparatus comprising first and second members which periodically change a relative relationship in position, plural light emitting means, arranged at the first member, for respectively emitting lights in accordance with transmission data items, plural light receiving means, arranged at the second member, for receiving lights emitted from the plural light emitting means, and means for switching the transmission data items supplied to the plural light emitting means in synchronism with a change of a relative relationship in position between the first and second members, thereby predetermined transmission data items are received by predetermined light receiving means irrespective of the relative relationship in position between the first and second members.

According to still another aspect of the present invention, there is provided an optical data transmission apparatus comprising first and second members which periodically change a relative relationship in position, plural light emitting means, arranged at the first member, for respectively emitting lights in accordance with transmission data items, plural light receiving means, arranged at the second member, for receiving lights emitted from the plural light emitting means, and means for switching output signals from the light receiving means in synchronism with a change of a relative relationship in position between the first and second members, thereby predetermined transmission data items are output from predetermined light receiving means irrespective of the relative relationship in position between the first and second members.

According to an optical data transmission apparatus of the present invention, data can be transmitted with high reliability at a high speed in a simple construction by transmitting data by use of light between the first and second members whose positions are changed relative to each other. A large amount of data can be transmitted with high reliability in a simple construction by transmitting a plurality of data items by use of the plurality of light emitting means and light receiving means between the first and second members and selectively changing the transmission data to be supplied to the light receiving means in each period of change in the relative positions of the first and second members.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 6 is a view showing the arrangement of light emitting elements and light receiving elements of the second embodiment;

FIG. 8 is a diagram showing the relation between the interval between the light emitting elements and the interval between the light receiving elements in the second embodiment;

FIG. 9 is a diagram showing the operation effected for simultaneously transmitting two data items in the second embodiment;

FIG. 13 is a diagram showing the arrangement of light emitting elements and light receiving elements in the third embodiment;

FIG. 14 is a circuit diagram of a receiver circuit in the third embodiment; and

FIG. 15 is a signal waveform diagram of the receiver circuit in the third embodiment.

DETAILED DESCRIPTION OF THE PREFERRED EMBODIMENTS

A preferred embodiment of an optical data transmission apparatus according to the present invention will now be described with reference to the accompanying drawings. For convenience of explanation, an embodiment used for transmitting an X-ray control signal, X-ray detection signal or the like between the rotating portion and the fixed portion of an X-ray CT scanner is explained. However, the present invention can be applied to any type of data transmission apparatus for transmitting data between first and second members whose positions are changed relative to each other in a rotational or reciprocatory manner.

Figure 1:
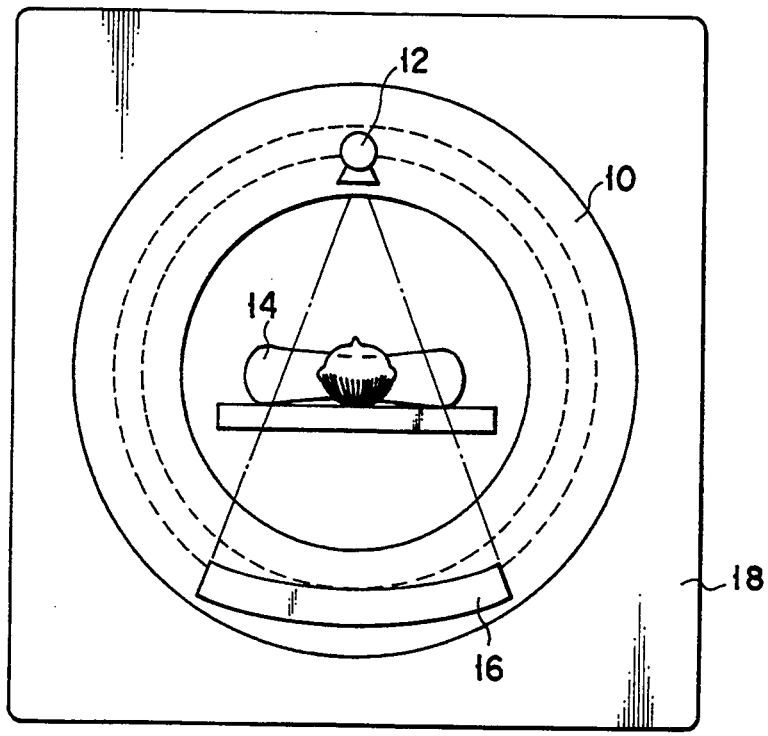
FIG. 1 is a view schematically showing a first embodiment of an optical data transmission apparatus according to the present invention.

FIG. 1 is a schematic view of the first embodiment showing the gantry portion of the X-ray CT scanner as viewed from the front side. A central portion of a gantry (fixed portion) 18 is provided with a cylindrical opening. A rotating portion 10 having a doughnut shape housing is inserted into the cylindrical opening and is held to freely rotate in the cylindrical opening. The rotation axis of the rotating portion 10 is set in a direction perpendicular to the drawing or equal to the body axis of a patient. The rotating portion 10 includes an X-ray tube 12 for radiating an X-ray to the patient and a detector 16 for facing toward the X-ray tube 12 and for detecting the X-ray transmitted through the patient. The detector 16 is formed of plural detecting cells. Though a third-generation X-ray CT scanner is shown in FIG. 1, the present invention can be applied to any type of X-ray CT scanner. In the first embodiment, a drive voltage output from a high voltage power source is transmitted to the rotating portion (X-ray tube 12) via a slip ring, in the same manner as in the conventional scanner. X-ray detection data is transmitted to the fixed portion (a data acquisition system and an image reconstruction circuit) via an optical data transmission apparatus according to the present invention.

Figure 2:
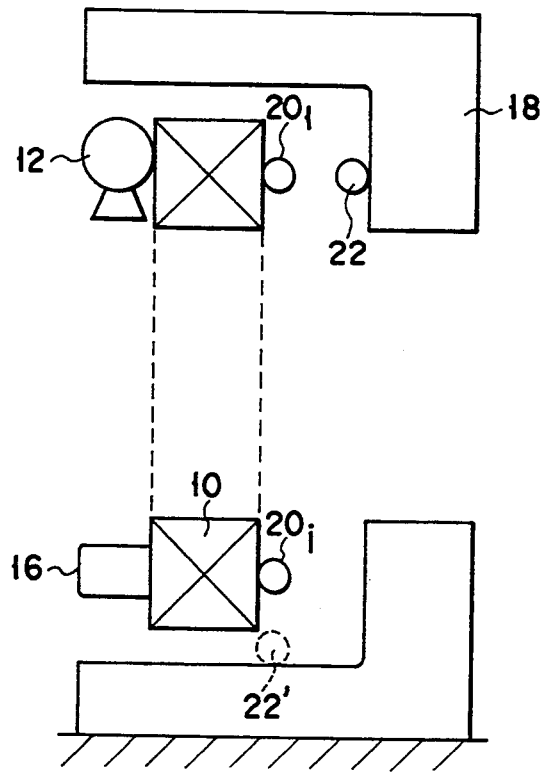
FIG. 2 shows a main portion of the first embodiment.
Figure 3:
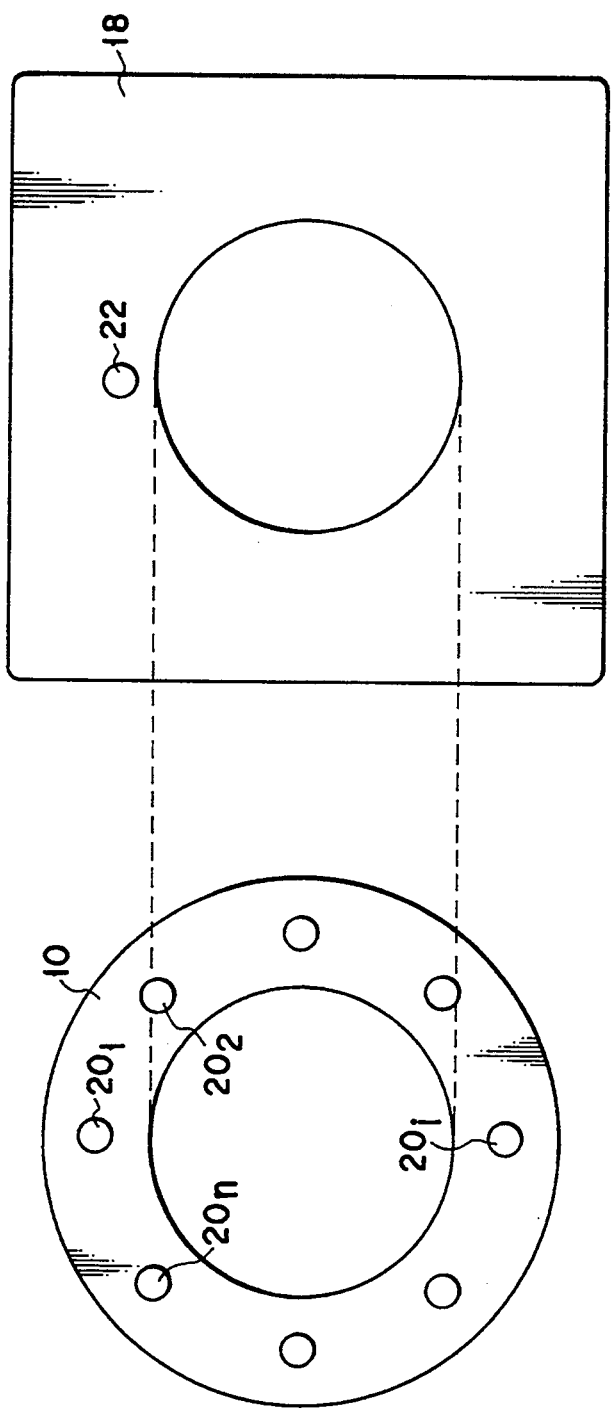
FIG. 3 is a view showing the arrangement of a light emitting element and light receiving elements of the first embodiment.

FIG. 2 is a side view of the gantry of the X-ray CT scanner explaining the principle of the optical data transmission apparatus. FIG. 3 is a view showing the optical data transmission apparatus by developing a construction shown in FIG. 2 at a boundary between the rotating portion 10 and the gantry 18. A large number of light emitting elements (for example, light emitting diodes) $20_1, 20_2, \ldots 20_n$ are arranged at a regular interval on one of side surfaces or surfaces perpendicular to the rotating axis (which faces the gantry 18) of the housing of the rotating portion 10. A light receiving element (for example, photodiode) 22 is arranged on one of side surfaces or surfaces perpendicular to the rotating axis (which faces the rotating portion 10) of the gantry 18. The light emitting elements $20_1, 20_2, \ldots 20_n$ simultaneously emit light in accordance with the output of the detector 16. It is desirable for the light emitting elements to emit infrared light so that data transmission will not be influenced by the environment light. Though not shown in the drawing, it is desirable to provide a guide of an arc shape along the arrangement of the light emitting elements so that light is not spread in the radial direction of the rotating portion 10. The number "n" of the light emitting elements 20 is determined according to the length of the periphery of the housing of the rotating portion 10, a gap between the peripheral surface of the housing of the rotating portion 10 and the wall surface of the hole of the gantry 18, and a directivity of the light emitting element and light receiving element such that the light receiving element 22 can receive light emitted from one or two light emitting elements during the rotation of the rotating portion 10. As a result, reception of the transmission data on the light receiving element 22 is not interrupted even if the rotating portion 10 is continuously rotated.

Since the light emitting element and light receiving elements are provided on the side surfaces or flat surfaces not the cylindrical surfaces, manufacturing of the apparatus is easy.

Since the light emitting elements 20 are arranged to directly apply light to the light receiving element 22 and the light emitting elements 20 of a number which is large enough to prevent light received by the light receiving element 22 from being interrupted during the rotation are provided, the light emitting elements 20 can be disposed close to the light receiving element 22. Thus, a distance between the light emitting element and the light receiving element can be set short, optical means such as light converging means is not necessary, thereby making the construction of an optical system simple, and since the efficiency of usage of light is high, the apparatus can be realized by use of inexpensive light emitting diodes.

Further, since non-contact data transmission is effected by use of light as a transmission medium, periodic maintenance for which part replacement must be effected and which is indispensable in the conventional slip ring system can be omitted, any problem due to poor contact and contact resistance will not occur, and data transmission quality and reliability can be enhanced. Since data is transmitted by use of light, the data transmission speed is enhanced and time for data transmission is reduced. Further, since any influence due to electromagnetic noise will not occur, the transmission precision becomes high.

According to the first embodiment, there is provided an optical data transmission apparatus which is suitable for an X-ray CT scanner.

In the first embodiment, it is possible to use a single light emitting element instead of a plurality of light emitting elements and dispose a plurality of light receiving elements in an annular form. The present invention can be applied to the data transmission from the gantry 18 to the rotating portion 10. Further, though both the light emitting element and the light receiving element are provided on the flat surfaces in the above description, it is possible to arrange the plural elements on the flat surfaces and the single element on a surface other than the flat surfaces, e.g., at a location 22' shown in FIG. 2. It is not so difficult to arrange the single element on the cylindrical surface.

Since the single light receiving element 22 is used and all of the light emitting elements 20 are simultaneously driven based on the same transmission data in the first embodiment, the number of transmission data channel is one. Next, a second embodiment in which a plurality of transmission channels are provided to simultaneously transmit a plurality of data items and the transmission efficiency is enhanced is explained. The second embodiment is formed of the rotating portion and the fixed portion as in the first embodiment. However, two data items are transmitted from the rotating portion to the fixed portion and also from the fixed portion to the rotating portion.

Figure 4:
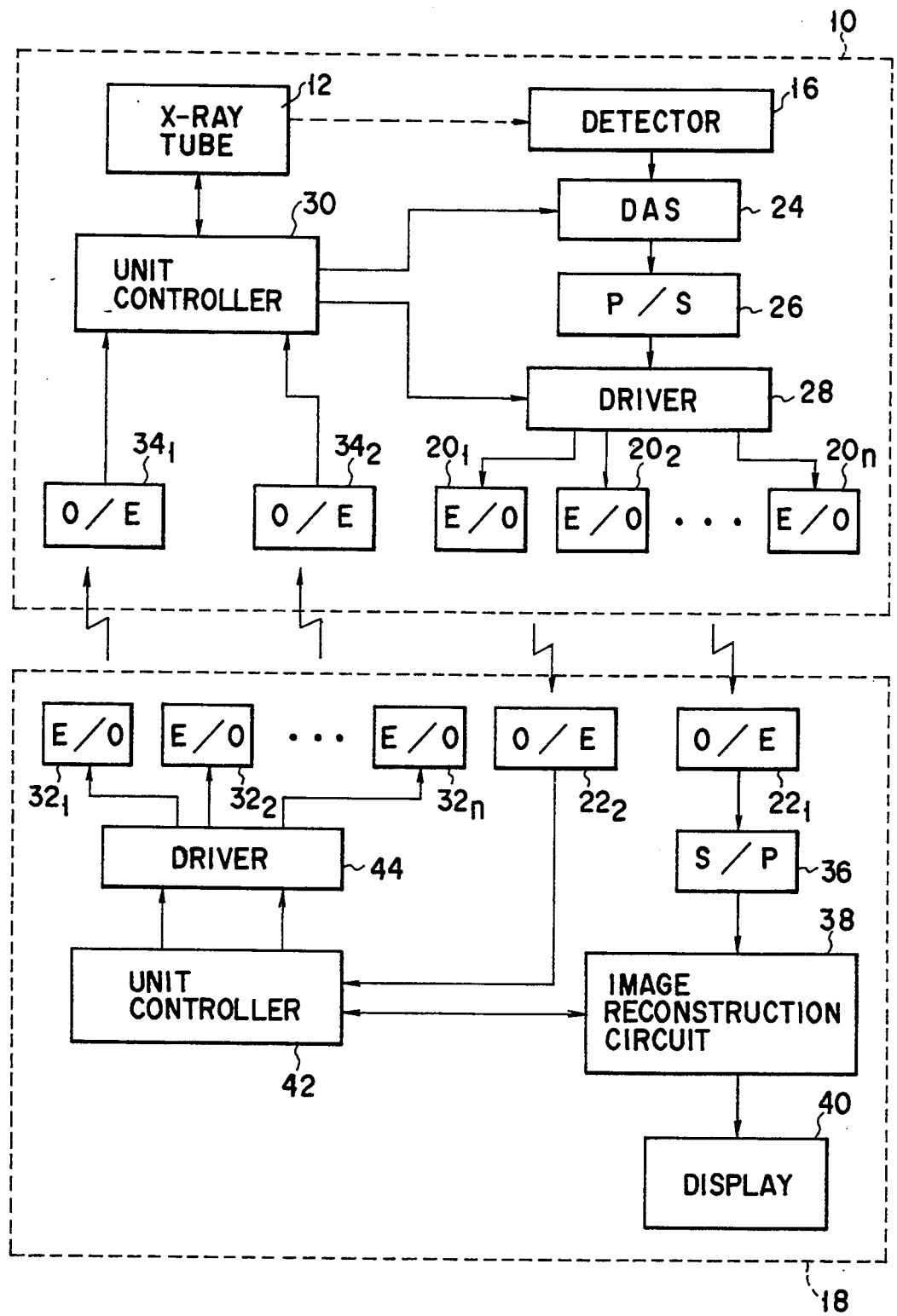
FIG. 4 is a block diagram showing the construction of a second embodiment of an optical data transmission apparatus according to the present invention.

FIG. 4 is a block diagram showing the circuit construction of an X-ray CT scanner to which the second embodiment of the present invention is applied. An output from each of the channels of the detector 16 is collected by a data acquisition system (DAS) 24 and then supplied to a parallel/serial (P/S) converter 26 as a parallel digital signal. Serial data output from the P/S converter 26 is supplied to a switching unit/driver 28. The light emitting elements $20_1, 20_2, \ldots 20_n$ are driven by the switching unit/driver 28. In the rotating portion 10, a unit controller 30 for controlling respective units of the rotating portion and an output of the unit controller 30 is supplied to the X-ray tube 12, DAS 24, and switching unit/driver 28. The switching unit/driver 28 divides a plurality of light emitting elements (electro-optical converting elements; E/O) $20_1, 20_2, \ldots 20_n$ into a plurality of groups each containing a preset number of light emitting elements and drives each of the light emitting element groups according to one of first and second transmission data items. The first and second transmission data items are switched in synchronism with the rotation of the rotating portion 10. Thus, two transmission channels are provided from the rotating portion 10 to the fixed portion 18. In this embodiment, an X-ray detection signal from the detector 16 is transmitted via one channel and various control signals from the unit controller 30 are transmitted via the other channel.

Figure 5:
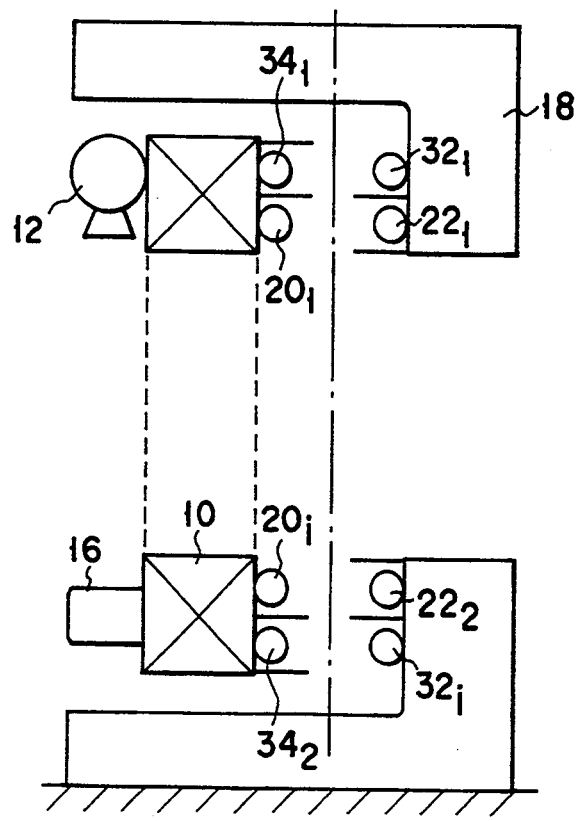
FIG. 5 shows a main portion of the second embodiment.

As in the first embodiment, light is radiated in the axial direction. For this purpose, a large number of light emitting elements $20_1, 20_2, \ldots 20_n$ are disposed on the side surface of the rotating portion 10 at a regular interval and two light receiving elements (opto-electrical converting elements; O/E) $22_1$ and $22_2$ for receiving lights of first and second transmission data are mounted on the side surface of the gantry 18 which faces the side surface of the rotating portion 10, as shown in FIGS. 5 and 6. The light receiving elements $22_1$ and $22_2$ are disposed with a phase deviation of 180°. Further, for data transmission from the fixed portion 18 to the rotating portion 10, a large number of light emitting elements $32_1, 32_2, \ldots 32_n$ are arranged at a regular interval on the side surface of the fixed portion 18 and two light receiving elements $34_1$ and $34_2$ for receiving lights of first and second transmission data are mounted with a phase deviation of 180° on the side surface of the rotating portion 10 which faces the side surface of the fixed portion. Outputs of the light receiving elements $34_1$ and $34_2$ are supplied to the unit controller 30. FIG. 6 indicates the data transmission from the rotating portion 10 to the fixed portion 18.

Figure 7:
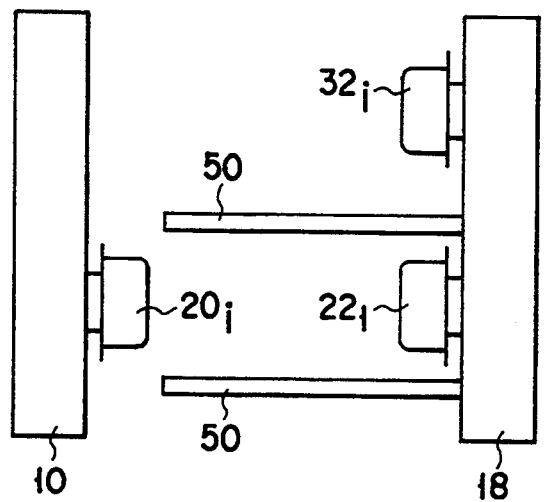
FIG. 7 is a view showing a hood attached to the light receiving element.

FIG. 7 shows the light emitting elements and light receiving elements in detail. As the light emitting element 20 or 32, a light emitting element having small directivity is used so that the light radiation plane may spread in the circumferential direction as shown in FIG. 8. FIG. 8 is a top view of the gantry. Since the reduced amount of light power emitted from the element whose directivity is small is generally large, it is necessary to set a distance between the light emitting element and the light receiving element to be less than several centimeters. Further, in order to prevent the light diffusion in a direction other than the circumferential direction and interrupt the light from the light emitting element 32 or 20 used for transmission in a reverse direction, it is preferable to attach a hood 50 to the light receiving element 22 or 34. The surface of the hood 50 may be of any kind if it has a large reflecting power. Further, the hood 50 also serves as a means for interrupting external light, e.g., a room illumination. As shown in FIG. 8, the light receiving element 22 or 34 is formed of two elements 22a and 22b.

Thus, a plurality of light emitting elements and light receiving elements are driven to make groups for light emission and light reception, and therefore, data transmission will not be influenced even when any one of the light emitting elements and light receiving elements is damaged. For example, in the case of FIG. 8, data transmission can be effected even if one of the light receiving elements 22a and 22b is damaged and two light emitting elements $20_{i-1}$ and $20_{i+1}$ which are not adjacent to each other are damaged in the worst case. Therefore, the reliability of the whole system can be enhanced.

In order to prevent data transmission from being interrupted during the rotation of the rotating portion 10, the interval between the light emitting elements 20 or 32 and a distance between the rotating portion 10 and the fixed portion 18 are set in the same manner as in the first embodiment so that the illumination areas of the light emitting elements 20 or 32 may partly overlap each other on the light receiving element 20 or 32.

First transmission data output from the light receiving element $22_1$ is converted into parallel digital data by an S/P converter 36 and then input to an image reconstruction circuit 38 as X-ray detection data (projection data). An image reconstructed by the image reconstruction circuit 38 is displayed on a display unit 40. A unit controller 42 for controlling each unit of the fixed portion 18 is provided in the fixed portion 18 and second transmission data output from the light receiving element $22_2$ is supplied to the unit controller 42.

The unit controller 42 supplies two data items to be transmitted from the fixed portion 18 to the rotating portion 10 to a switching unit/driver 44. The switching unit/driver 44 divides a plurality of light emitting elements $32_1, 32_2, \ldots 32_n$ into a plurality of groups each containing a preset number of light emitting elements and drives each of the light emitting element groups according to one of first and second transmission data items. The first and second transmission data items are switched in synchronism with the rotation of the rotating portion 10. Thus, two transmission channels are provided from the fixed portion 18 to the rotating portion 10. In this case, various control signals are transmitted from the fixed portion 18 to the rotating portion 10 by use of two channels.

Next, the operation of simultaneously transmitting two data items in this embodiment is explained. For convenience of explanation, a case wherein data is transmitted from the rotating portion 10 to the fixed portion 18 is explained. It is assumed that a large number of light emitting elements 20 arranged on the side surface of the rotating portion 10 in an annular form are divided into twelve light emitting element groups $T_1$ to $T_{12}$ as shown in FIG. 9. The switching unit/driver 28 separately drives each of the groups $T_i$ and transmits individual signals to the light receiving elements $22_1$ and $22_2$ on the fixed portion 18 side. However, since those of the light emitting elements which can apply lights to the light receiving elements $22_1$ and $22_2$ are changed with rotation of the rotating portion 10, it becomes necessary to change data supplied to the light emitting element group $T_i$ in synchronism with rotation of the rotating portion 10. In order to detect the rotation angle of the rotating portion 10, an optical sensor 56 is attached to the rotating portion 10 and slits $S_1$ to $S_{12}$ used for driving the optical sensor 56 are arranged on the fixed portion 18 side. That is, the optical sensor 56 outputs a detection pulse each time it passes the slit position. Although not shown in the drawing, the detection pulse is supplied to the switching unit/driver 28.

Figure 10:
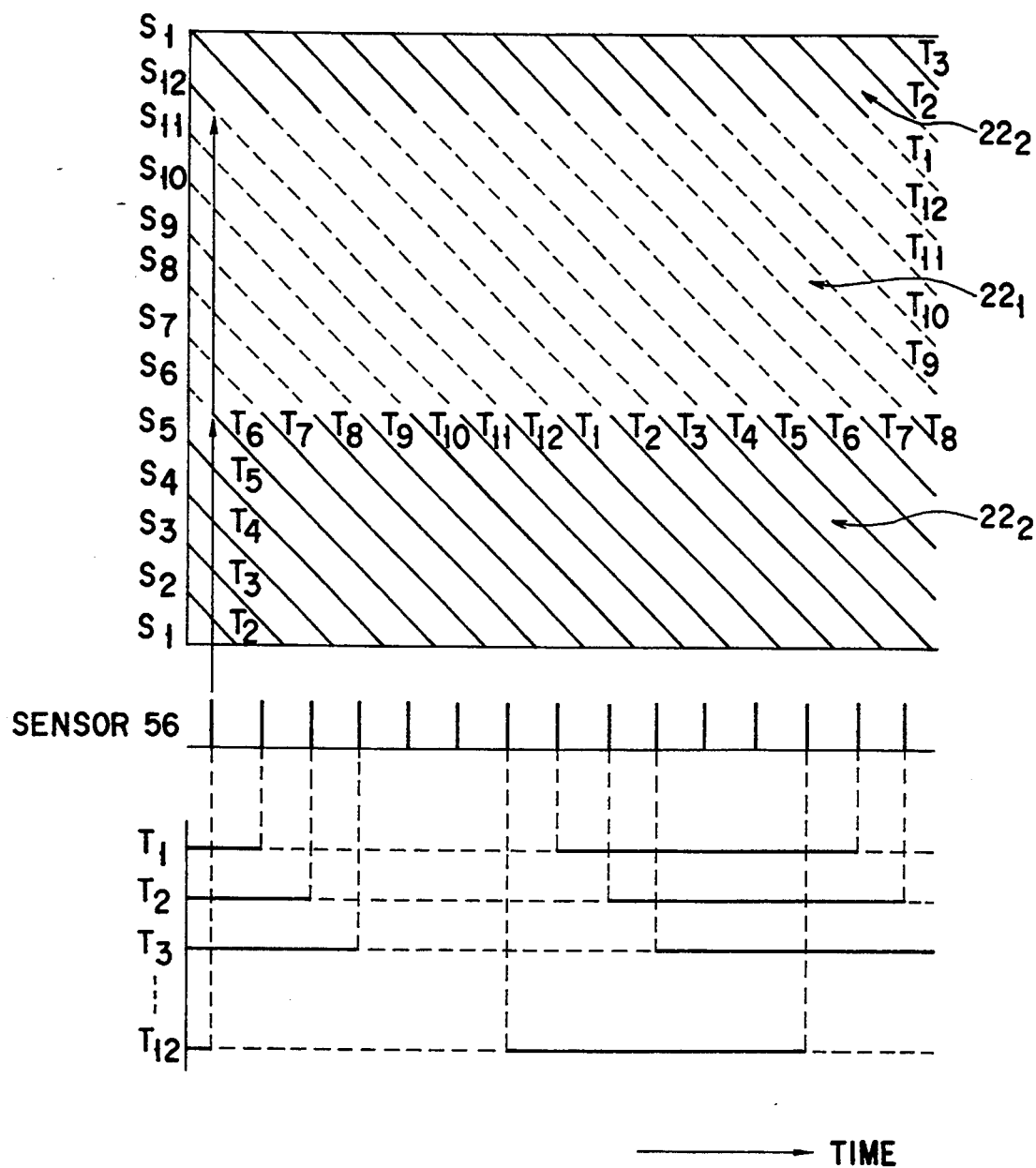
FIG. 10 is a diagram showing switching timings for the light emitting elements and light receiving elements in the operation of the second embodiment.

FIG. 10 shows a condition in which transmission data supplied to the respective light emitting elements is changed. Transmission data for each of the light emitting elements $T_1$ to $T_{12}$ is changed each time the rotating portion 10 makes a half revolution (that is, each time six detection pulses are output from the optical sensor 56). For example, the light emitting element group $T_1$ is supplied with transmission data (second transmission data) to be transmitted to the light receiving element $22_2$ in response to the second detection pulse output and emits light corresponding to the second transmission data when it passes a position facing the light receiving element $22_2$. After this, the transmission data is switched to transmission data (first transmission data) for the light receiving element $22_1$ in response to an eighth detection pulse and the light emitting element group emits light corresponding to the first transmission data when it passes a position facing the light receiving element $22_1$. Thus, the light emitting elements $T_1, T_2, \ldots T_{12}$ selectively change the transmission data in response to the rotation detection pulse from the sensor 56 so that predetermined signals may be always transmitted to the light receiving elements $22_1$ and $22_2$. The upper portion of FIG. 10 shows time on the abscissa and the movement of the rotating portion when viewed from the fixed portion side on the ordinate. Each of the light emitting element groups shown in the lower portion of FIG. 10 emits a light of data to be transmitted to the light receiving element $22_1$ in positions indicated by solid lines and emits a light of data to be transmitted to the light receiving element $22_2$ in positions indicated by broken lines.

As described above, according to the second embodiment, the effect that the data transmission speed is enhanced by increasing the number of data items which can be simultaneously transmitted and the mounting space is not increased even if the number of transmission channels is increased can be obtained in addition to the effect obtained in the first embodiment. Further, in the above description, all of the light emitting elements lying in the range from the rotation position of the slit $S_5$ to the rotation position of the slit $S_{11}$ emit lights according to the first transmission data and all of the light emitting elements lying in the range from the rotation position of the slit $S_{11}$ to the rotation position of the slit $S_5$ emit lights according to the second transmission data. However, in practice, only the light emitting elements lying in the range from the rotation position of the slit $S_3$ to the rotation position of the slit $S_1$ or from the rotation position of the slit $S_9$ to the rotation position of the slit $S_7$ contribute to the data transmission. Therefore, it is possible to reduce the power consumption by deactivating the light emitting elements which lie in a rotation position range other than the above rotation position range and do not contribute to the data transmission.

Figure 11:
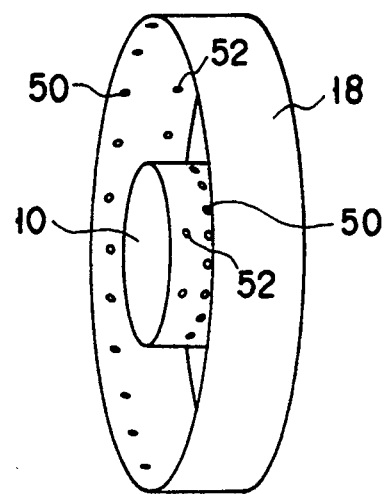
FIG. 11 is a view showing a modification in which the light transmission direction in the second embodiment is changed.

The second embodiment can be modified in the same manner as in the first embodiment. That is, it is possible to use light emitting elements which number corresponds to the number of data transmission channels and dispose a plurality of light receiving elements in an annular form. It is possible to arrange the light receiving elements of FIG. 6 on a surface other than the flat surfaces, e.g., at a location 22' shown in FIG. 2. Further, since the second embodiment is characterized by provision of plural data transmission channels and thus the light transmission direction is not limited to the axial direction. It is possible to set the light transmission direction to correspond to the radial direction of the rotating portion in the same manner as in the first embodiment by mounting the light receiving elements 52 and the light emitting elements 50 on the circumferential cylindrical surfaces as shown in FIG. 11 and arrange the light emitting and receiving elements to face each other in the radial direction. A hood is omitted in FIG. 11.

Further, the rotation angle of the rotating portion 10 may be detected by use of an exclusive rotary encoder or detected by using rotation position data supplied from an external unit which has information on the rotation position. For convenience of explanation, a case wherein two data items are transmitted is explained, but when it is required to transmit more data items, the light emitting elements may be more finely divided or the timings for transmission data change may be more finely set. With this modification, it becomes possible to transmit data items of up to a number corresponding to half the number of the light emitting elements. In order to simultaneously transmit a plurality of data items, it is necessary to provide light receiving elements of the same number as that of transmission data items.

In the above embodiments, a variation in the level of the transmission signal may occur during the rotation of the rotating portion 10. This is because the level of the light signal received by the light receiving element varies according to a variation in the relative positional relation between the light emitting element and the light receiving element. That is, the transmission signal is subjected to amplitude modulation according to the rotation of the rotating portion. In order to cope with the above amplitude modulation, it is generally required for the receiver circuit to have a wide dynamic range. However, the dynamic range is in the trade-off relation with respect to an S/N ratio and it is difficult to attain a wide dynamic range while keeping an S/N ration high in the prior art.

Therefore, a third embodiment in which a variation in the signal level caused by the rotation of the rotating portion can be coped with without increasing the dynamic range is explained below. For convenience of explanation, a case wherein the light emitting elements and the light receiving elements are arranged on the cylindrical surfaces along the rotating axis and the light transmission direction is the radial direction is described. However, it is possible to set the light transmission direction to correspond to the axial direction in the same manner as in the first and second embodiments.

Figure 12:
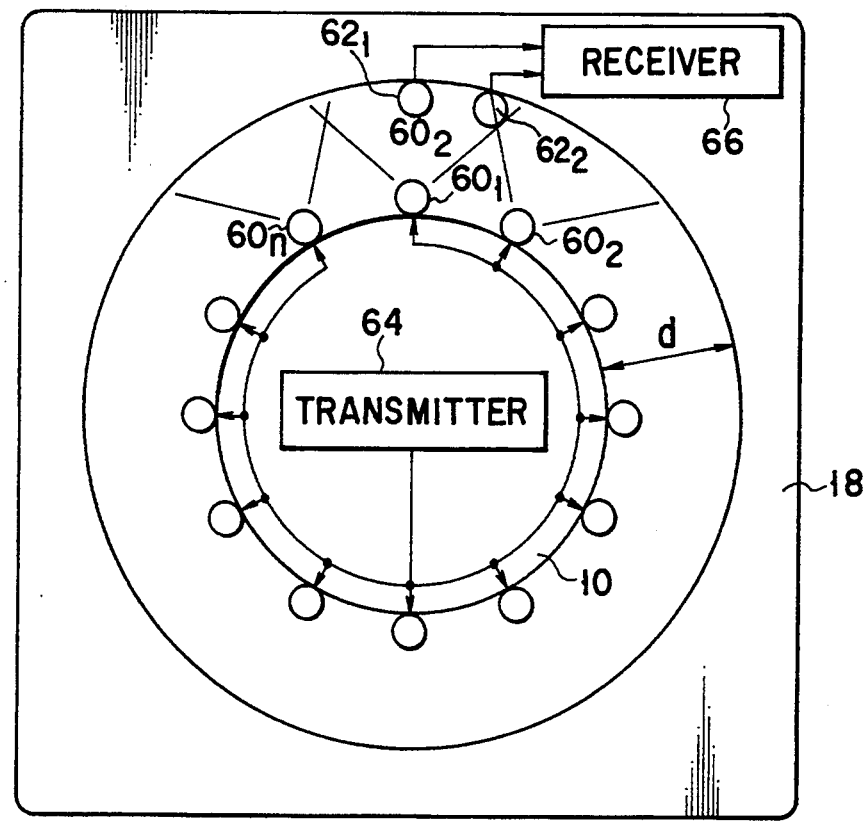
FIG. 12 is a view schematically showing a third embodiment of an optical data transmission apparatus according to the present invention.

FIG. 12 is a schematic view showing the third embodiment which is similar to the first embodiment shown in FIG. 1 in most portions and different from the first embodiment only in that a plurality of (in this example, two) light receiving elements $62_1$ and $62_2$ are provided in the fixed portion 18. Unlike the second embodiment, the light receiving elements $62_1$ and $62_2$ are disposed adjacent to each other and light emitting elements $60_1, 60_2, \ldots 60_n$ are activated by a transmitter 64 in accordance with the same transmission data. That is, a plurality of light receiving elements are provided, but a single transmission channel is used.

A distance between the two light receiving elements $62_1$ and $62_2$ is equal to a half (or odd multiple) of the distance D between the light emitting elements $60_1, 60_2, \ldots 60_n$ which are arranged at a regular interval on the peripheral surface of the rotating portion 10 as shown in FIG. 13. Therefore, when one light receiving element $62_1$ is set to face a given light emitting element $60_{i-1}$, the other light receiving element $62_2$ is set in the intermediate position between the two adjacent light emitting elements $60_{i-1}$ and $60_i$ or $60_i$ and $60_{i+1}$. That is, when one light receiving element $62_1$ is in an in-phase position with respect to the light emitting element, the other light receiving element $62_2$ is in a 180° out-of-phase position with respect to the light emitting element.

As shown in FIG. 14, outputs of the light receiving elements $62_1$ and $62_2$ are combined to create a single reception signal in the receiver 66. Light signals from the light emitting elements $60_1, 60_2, \ldots 60_n$ which are activated according to transmission data are received by the light receiving elements $62_1$ and $62_2$ and converted into current signals $i_{s1}$ and $i_{s2}$. The current signals $i_{s1}$ and $i_{s2}$ are input to a current/voltage converting amplifier $A_1$ having an adding function. It is assumed that the feedback resistance is $R_f$, then an output $v_s$ of the amplifier $A_1$ is set to $R_f(i_{s2}+i_{s2})$. The output $V_s$ is compared with a reference voltage $v_{ref}$ in a succeeding stage comparator $A_2$ and converted into a digital signal. Further, it is also possible to effect the current/voltage conversion for each of the light receiving elements, then add reception signals thus obtained and convert the added signal into a digital signal.

Since the phases of the light receiving elements $62_1$ and $62_2$ with respect to the light emitting element are shifted by 180°, the output current signals $i_{s1}$ and $i_{s2}$ of the light receiving elements $62_1$ and $62_2$ vary in the sinusoidal form during the rotation of the rotating portion 10 as shown in FIG. 15. The period of the sine wave is equal to the distance D/2 between the light emitting elements 60. In this case, as shown in FIG. 13, since the light receiving elements $62_1$ and $62_2$ have a phase difference of 180°, one of the output signals becomes minimum when the other output signal becomes maximum. Therefore, the output $v_s$ of the amplifier $A_1$ for adding the above two output signals together becomes equal to a mean value of the above two output signals and is set at a constant level.

Thus, outputs of the light receiving section can be averaged by deriving a mean value of the outputs of the two light receiving elements and the amplitude modulation thereof can be suppressed, thereby making it possible to effect the current/voltage conversion with an optimum gain. Therefore, it becomes unnecessary to increase the dynamic range, and as a result, an S/N ratio can be enhanced, a bit error due to noise occurring at the time of generation of low level signal can be prevented, and the bit error rate which corresponds to the reliability of data transmission can be improved.

As described above, according to the third embodiment, irrespective of a change in the relative positional relation between the light emitting elements and the light receiving elements according to the rotation of the rotating portion, the output of the light receiving section can always be kept constant and correct data can be transmitted.

When the third embodiment is applied to the second embodiment, each of the light receiving elements $22_1$, $22_2$, $34_1$, and $34_2$ may be constructed by two light receiving elements.

As described above, according to the present invention, an optical data transmission apparatus which is simple in construction and which can transmit a large amount of data with high reliability.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, a case wherein the present invention is applied to the X-ray CT scanner is explained, the present invention is not limited to the X-ray CT scanner. Further, the present invention is not limited to data transmission between the rotating portion and the fixed portion, but may be applied to data transmission between two members whose positions are changed relative to each other. In the third embodiment, the two light receiving elements are arranged to attain a phase difference of 180° between the outputs thereof as shown in FIG. 13, but the phase difference is not necessarily limited to 180° and may be set to a value which is somewhat deviated from 180° since the influence by a level variation can be reduced to some extent even when the phase of the outputs are deviated from each other. That is, the distance between the light receiving elements $62_1$ and $62_2$ may not be necessarily set to nD/2 (n is an odd number).

What is claimed is:

1. An optical data transmission apparatus comprising:
first and second members at least one of which rotates to change a relative relationship in position and which respectively have first and second planes perpendicular to a rotation axis;
light emitting means, arranged at the first plane of said first member, for emitting light in accordance with transmission data, said light emitting means comprising light emitting elements for emitting lights in accordance with said transmission data;
light receiving means, arranged at the second plane of said second member, for receiving light emitted form said light emitting means, said light receiving means comprising two light receiving elements for receiving lights emitted from the light emitting elements, and means for adding together outputs from the two light receiving elements; and
wherein said light emitting elements are arranged at an interval D, and said two light receiving elements are arranged at an interval nD/2, with n being an odd number.

2. An apparatus according to claim 1, wherein said light emitting means emits light in a direction other than a direction perpendicular to the rotation axis.

3. An apparatus according to claim 2, wherein said light emitting means emits light in a direction parallel to the rotation axis.

4. An apparatus according to claim 1, wherein said first member is a rotating portion of a gantry of an X-ray computerized tomography scanner and said second member is a fixed portion of the gantry.

5. An apparatus according to claim 1, wherein said first member is a fixed portion of a gantry of an X-ray computerized tomography scanner and said second member is a rotating portion of the gantry.

6. An apparatus according to claim 1, wherein said light emitting means comprises light emitting elements which are arranged at a regular interval so that said light receiving means receives light from at least one of the light emitting elements.

7. An apparatus according to claim 1, wherein said light emitting means comprises light emitting elements for respectively emitting lights in accordance with transmission data items;
said light receiving means comprises light receiving elements for respectively receiving lights emitted from the light emitting elements; and
said light emitting means further comprises means for switching the transmission data items supplied to the light emitting elements in synchronism with a change of a relative relationship in position between said first and second members, thereby predetermined transmission data items are received by predetermined light receiving elements irrespective of the relative relationship in position between said first and second members.

8. An apparatus according to claim 1, wherein said light emitting means comprises light emitting elements for respectively emitting lights in accordance with transmission data items; and
said light receiving means comprises light receiving elements for respectively receiving lights emitted from the light emitting elements, and means or switching output signals from the light receiving elements in synchronism with a change of a relative relationship in position between said first and second members, thereby predetermined transmission data items are output from predetermined light receiving elements irrespective of the relative relationship in position between said first and second members.

9. An optical data transmission apparatus comprising:
first and second members at least one which rotates to change a relative relationship in position;
light emitting means, arranged at a plane of said first member which is perpendicular to a rotation axis, for emitting light in accordance with transmission data, said light emitting means comprising light emitting elements for emitting lights in accordance with said transmission data;

light receiving means, arranged at a plane of said second member other than a plane which is perpendicular to the rotation axis, for receiving light emitted form said light emitting means, said light receiving means comprising two light receiving elements for receiving lights emitted form the light emitting elements, and means for adding together outputs from the two light receiving elements; and wherein said light emitting elements are arranged at an interval D, and said two light receiving elements are arrange at an interval nD/2, with n being an odd number.

10. An apparatus according to claim 9, wherein said light emitting means emits light in a direction other than a direction perpendicular to the rotation axis.

11. An apparatus according to claim 9, wherein said light emitting means comprises light emitting elements which are arranged at a regular interval so that said light receiving means receives light from at least one of the light emitting elements.

12. An optical data transmission apparatus comprising:

first and second members at least one of which rotates to change a relative relationship in position;

light emitting means, arranged at a plane of said first member other than a plane which is perpendicular to a rotation axis, for emitting light in accordance with transmission data, said light emitting means comprising light emitting elements for emitting lights in accordance with said transmission data;

light receiving means arranged at a plane of said second member which is perpendicular to the rotation axis, for receiving light emitted from said light emitting means, said light receiving means comprising two light receiving elements for receiving lights emitted from the light emitting elements, and means for adding together outputs from the two light receiving elements; and wherein said light emitting elements are arranged at an interval D, and said two light receiving elements are arranged at an interval nD/2, with n being an odd number.

13. An apparatus according to claim 12, wherein said light emitting means emits light in a direction other than a direction perpendicular to the rotation axis.

14. An apparatus according to claim 12, wherein said light emitting means comprises light emitting elements which are arranged at a regular interval s that said light receiving means receives light from at lest one of the light emitting elements.

15. an optical data transmission apparatus comprising:

first and second members at least one of which rotates to change a relative relationship in position;

light emitting means, arranged at said first member, for emitting light in accordance with transmission data in a direction other than a direction perpendicular to the rotation axis, said light emitting means comprising light emitting elements for emitting light in accordance with said transmission data;

light receiving means, arranged at said second member, for receiving light emitted from said light emitting means, said light receiving means comprising two light receiving elements for receiving lights emitted from the light emitting elements, and means for adding together outputs from the two light receiving elements; and wherein said light emitting elements are arranged at an interval D, and said two light receiving elements are arranged at an interval nD/2, with n being an odd number.

16. An apparatus according to claim 15, wherein said light emitting means emits light in a direction other than a direction perpendicular t the rotation axis.

17. An apparatus according to claim 15, wherein said light emitting means comprises light emitting elements which are arranged at a regular interval so that said light receiving means receives light from at least one of the light emitting elements.

18. An optical data transmission apparatus comprising:

first and second members which periodically change a relative relationship in position;

plural light emitting means, arranged at said first member, for respectively emitting lights in accordance with transmission data items, each of said plural light emitting means comprising plural light emitting elements for emitting lights in accordance with said transmission data;

plural light receiving means, arranged at said second member, for receiving lights emitted from said plural light emitting means, said light receiving means comprising two light receiving elements for receiving lights emitted from each of said plural light emitting means, and means for adding together outputs from the two light receiving elements;

means for switching the transmission data items supplied to said plural light emitting means in synchronism with a change of a relative relationship in position between said first and second members, thereby permitting predetermined transmission data items to be received by predetermined light received means irrespective of the relative relationship in position between said first and second members; and wherein said light emitting elements are arranged at an interval D, and said two light receiving elements are arranged at an interval nD/2, with n being an odd number.

19. An optical data transmission apparatus according to claim 18, wherein said first and second members at least one of which rotates to change a relative relationship in position;

said plural light emitting means are arranged at a plane of said first member which is perpendicular to a rotation axis; and said light receiving means is arranged at a plane of said second member which is perpendicular to the rotation axis.

20. An apparatus according to claim 19, wherein said plural light emitting means emit lights in a direction other than a direction perpendicular to the rotation axis.

21. An apparatus according to claim 19, wherein said plural light emitting means emit lights in a direction parallel to the rotation axis.

22. An apparatus according to claim 18, wherein said first member is a rotating portion of a gantry of an X-ray computerized tomography scanner and said second member is a fixed portion of the gantry.

23. An apparatus according to claim 18, wherein
said first member is a fixed portion of a gantry of an X-ray computerized tomography scanner and said second member is a rotating portion of the gantry.

24. An optical data transmission apparatus according to claim 18, wherein
said first and second members at least one of which rotates to change a relative relationship in position;
said plural light emitting means are arranged at a plane of said first member which is perpendicular to a rotation axis; and
said light receiving means is arranged at a plane of said second member other than a plane which is perpendicular to the rotation axis.

25. An optical data transmission apparatus according to claim 18, wherein
said firs and second members at least one of which rotates to change a relative relationship in position;
said plural light emitting means are arranged at a plane of said first member other than a plane which is perpendicular to a rotation axis; and
said light receiving means is arranged at a plane of said second member which is perpendicular to the rotation axis.

26. An optical data transmission apparatus comprising:
first and second members which periodically change a relative relationship in position;
plural light emitting means, arranged at said first member, for respectively emitting lights in accordance with transmission data items, each of said plural light emitting means comprising plural light emitting elements for emitting lights in accordance with said transmission data;
plural light receiving means, arranged at said second member, for receiving lights emitted from said plural light emitting means, said light receiving means comprising two light receiving elements for receiving lights emitted from each of said plural light emitting means, and means or adding together outputs from the two light receiving elements;
means for switching output signals from said light receiving means in synchronism with a change of a relative relationship n position between said first and second members, thereby predetermined transmission data items are output from predetermined light receiving means irrespective of the relative relationship in position between said first and second members; and wherein said light emitting elements are arranged at an interval D, and said two light receiving elements are arranged at an interval nD/2, with n being an odd number.

27. An optical data transmission apparatus according to claim 26, wherein
said first and second members at least one of which rotates to change a relative relationship in position;
said plural light emitting means are arranged at a plane of said first member which is perpendicular to a rotation axis; and
said light receiving means is arranged at a plane of said second member which is perpendicular to the rotation axis.

28. An apparatus according to claim 27, wherein
said plural light emitting means emit lights in a direction other than a direction perpendicular to the rotation axis.

29. An apparatus according to claim 28, wherein
said plural light emitting means emit lights in a direction parallel to the rotation axis.

30. An apparatus according to claim 26, wherein
said first member is a rotating portion of a gantry of an X-ray computerized tomography scanner and said second member is a fixed portion of the gantry.

31. An apparatus according to claim 26, wherein
said first member is a fixed portion of a gantry of an x-ray computerized tomography scanner and said second member is a rotating portion of the gantry.

32. An optical data transmission apparatus according to claim 26, wherein
said first and second members at least one of which rotates to change a relative relationship in position;
said plural light emitting means are arranged at a plane of said first member which is perpendicular to a rotation axis; and
said light receiving means is arranged at a plane of said second member other than a plane which is perpendicular to the rotation axis.

33. An optical data transmission apparatus according to claim 26, wherein
said first and second members at least one of which rotates to change a relative relationship in position;
said plural light emitting means are arranged at a plane of said first member other than a plane which is perpendicular to a rotation axis; and
said light receiving means is arranged at a plane of said second member which is perpendicular to the rotation axis.

* * * * *

UNITED STATES PATENT AND TRADEMARK OFFICE
CERTIFICATE OF CORRECTION

PATENT NO. : 5,336,897
DATED : August 09, 1994
INVENTOR(S) : Naofumi WATANABE et al It is certified that error appears in the above-indentified patent and that said Letters Patent is hereby corrected as shown below:

Claim 1, Column 12, Line 3 change "form" to --from--.

Claim 8, Column 12, Line 54 change "or" to --for--.

Claim 9, Column 13, Line 14 change "arrange" to --arranged--.

Claim 14, Column 13, Line 53 change "s" to --so--.

Claim 15, Column 13, Line 56 change "an" to --An--.
Column 13, Line 64 change "light" to --lights--.

Claim 16, Column 14, Line 10 change "t" to --to--.

Claim 18, Column 14, Line 41 change "received" to --receiving--.

Claim 25, Column 15, Line 17 change "firs" to --first--.

UNITED STATES PATENT AND TRADEMARK OFFICE
CERTIFICATE OF CORRECTION

PATENT NO.  : 5,336,897
DATED       : August 9, 1994
INVENTOR(S) : Naofumi Watanabe, et al It is certified that error appears in the above-indentified patent and that said Letters Patent is hereby corrected as shown below:

Claim 26, Column 15, Line 40 change "or" to --for--.
        Column 15, Line 44 change "n" to --in--.

Signed and Sealed this

Twenty-fifth Day of April, 1995

Attest:

BRUCE LEHMAN

Attesting Officer      Commissioner of Patents and Trademarks